US008547545B2

(12) United States Patent
Sasazawa et al.

(10) Patent No.: US 8,547,545 B2
(45) Date of Patent: Oct. 1, 2013

(54) METHOD AND APPARATUS FOR INSPECTING A SURFACE OF A SUBSTRATE

(75) Inventors: Hideaki Sasazawa, Kamisato (JP);
Takayuki Ishiguro, Kamisato (JP);
Kiyotaka Horie, Kamisato (JP); Yu Yanaka, Kamisato (JP)

(73) Assignee: Hitachi High-Technologies Corporation, Tokyo (JP)

( * ) Notice: Subject to any disclaimer, the term of this patent is extended or adjusted under 35 U.S.C. 154(b) by 120 days.

(21) Appl. No.: 13/210,418

(22) Filed: Aug. 16, 2011

(65) Prior Publication Data

US 2012/0081701 A1 Apr. 5, 2012

(30) Foreign Application Priority Data

Sep. 30, 2010 (JP) ................................. 2010-221889

(51) Int. Cl.
*G01N 21/88* (2006.01)
*G01N 21/55* (2006.01)
*G01N 21/47* (2006.01)

(52) U.S. Cl.
USPC .................. 356/237.2; 356/237.1; 356/237.3; 356/237.4; 356/237.5

(58) Field of Classification Search
USPC ..................................... 356/237.1–237.5, 394
See application file for complete search history.

(56) References Cited

U.S. PATENT DOCUMENTS

| 5,798,829 | A | * | 8/1998 | Vaez-Iravani | 356/237.1 |
| 6,157,444 | A | * | 12/2000 | Tomita et al. | 356/237.1 |
| 6,876,445 | B2 | | 4/2005 | Shibuya et al. | |
| 7,812,942 | B2 | * | 10/2010 | Moulin et al. | 356/237.2 |
| 7,898,652 | B2 | | 3/2011 | Hariyama et al. | |
| 2004/0207836 | A1 | * | 10/2004 | Chhibber et al. | 356/237.4 |
| 2009/0190123 | A1 | * | 7/2009 | Hariyama et al. | 356/237.2 |
| 2009/0262621 | A1 | * | 10/2009 | Saito et al. | 369/53.41 |

FOREIGN PATENT DOCUMENTS

| JP | 2000-180376 | 6/2000 |
| JP | 2006-352173 | 12/2006 |
| JP | 2009-180590 | 8/2009 |

* cited by examiner

*Primary Examiner* — Sang Nguyen
(74) *Attorney, Agent, or Firm* — Antonelli, Terry, Stout & Kraus, LLP.

(57) ABSTRACT

The present invention provides a method and apparatus for inspecting a surface of a substrate. The apparatus includes: a rotatable stage on which a substrate to be inspected is placed; an inspection optical system having an illumination light source for emitting light to a substrate placed on the stage and a detector for detecting light from the substrate which is irradiated with the light from the illumination light source; an A/D converter for amplifying and A/D converting signals output from the detector in the inspection optical system; and a defect detector for detecting defects in a surface of the substrate by processing signals output from the detector and converted by the A/D converter and classifying the defected defects. The defect detector extracts micro defects in the surface of the substrate by processing the signals output from the detector, and detects linear defects existing discretely in a linear region.

12 Claims, 6 Drawing Sheets

FIG. 5A
FIG. 5B
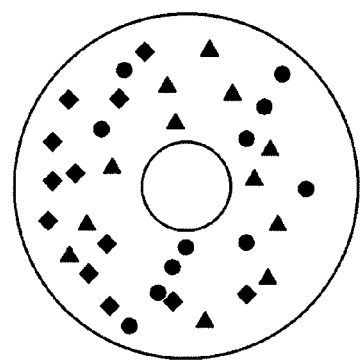
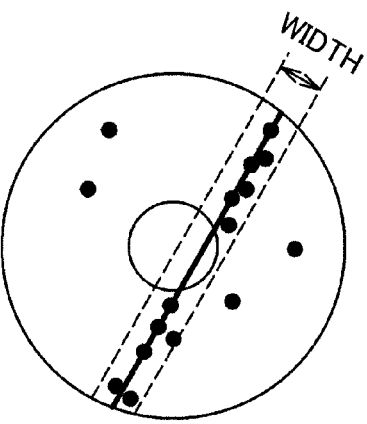
FIG. 6A
FIG. 6B
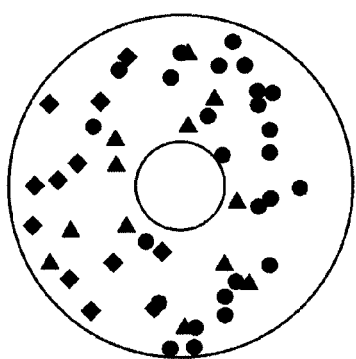
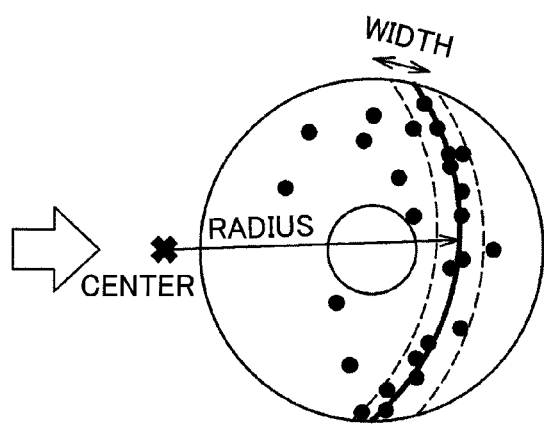

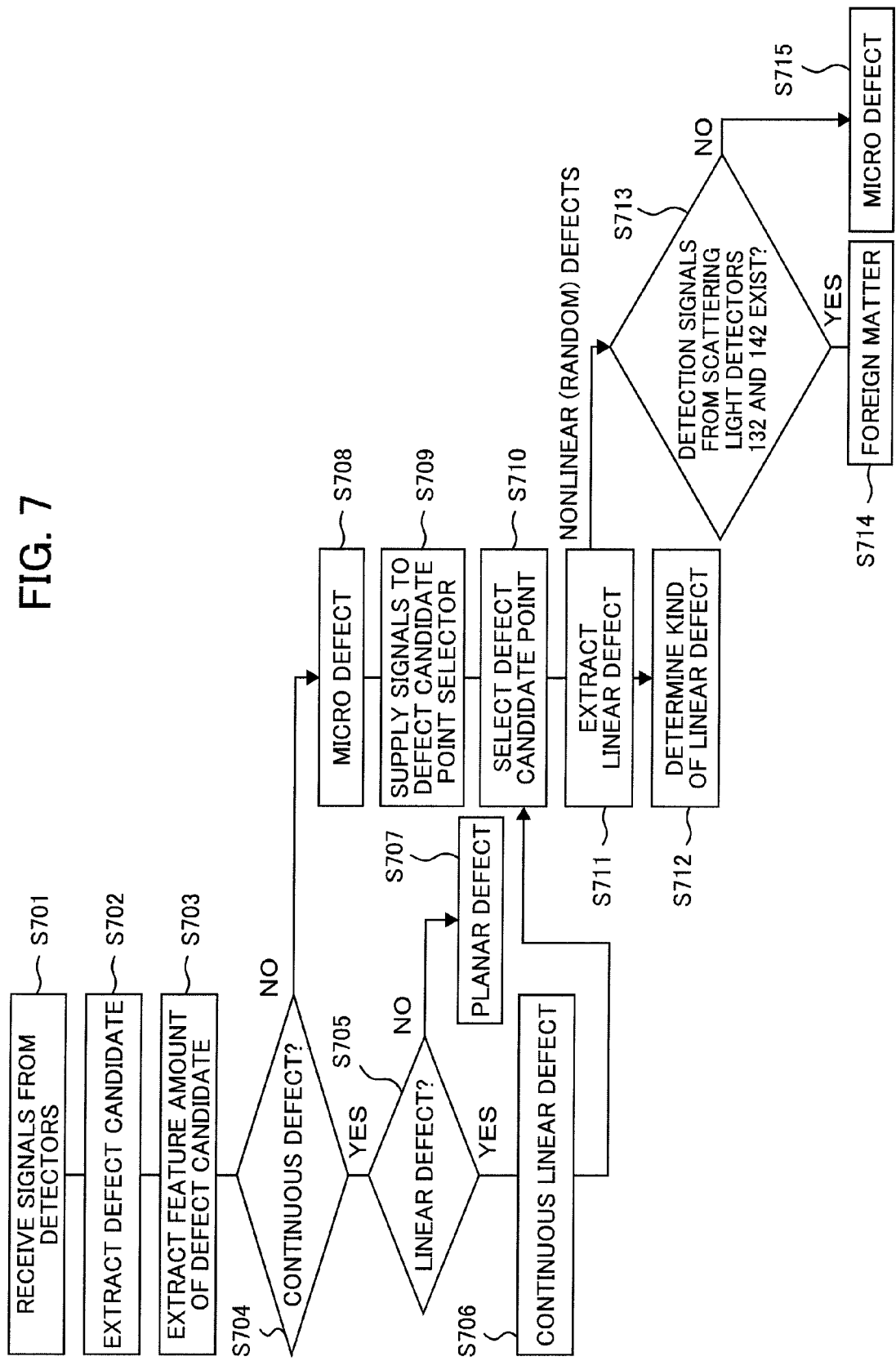

METHOD AND APPARATUS FOR INSPECTING A SURFACE OF A SUBSTRATE

BACKGROUND

The present invention relates to a method and apparatus for detecting a defect in a surface of a substrate and, more particularly, to a substrate surface inspecting method and apparatus suitable for detecting a linear defect in a surface of a magnetic disk substrate.

For an apparatus for inspecting a surface of a substrate for a magnetic disk, there is a need to classify detected defects in order to contribute to sophistication in process management and improvement in process. Generally, a detection optical system in an apparatus for inspecting a surface of a substrate for a magnetic disk includes plural detectors. In addition to classification of micro defects by detection signals from the plural detectors, classification of the defects on the basis of a feature to a distribution shape of the defects in a magnetic disk face is requested. Specifically, although continuous micro defects can be recognized as linear defects, defects distributed discretely and linearly (hereinbelow, written as a linear scratch defect) have to be discriminated from a collection of the other micro defects.

For example, Japanese Patent Application Laid-Open Publication No. 2000-180376 (patent document 1) discloses an apparatus for detecting a defect in a surface of a magnetic disk, which emits a laser beam to a magnetic disk as a sample to be inspected, receiving reflection light and scattering light from the surface of the magnetic disk by plural detectors, and classifying micro defects in accordance with light reception conditions of light receivers of the detectors. By determining continuity in a plane of the detected micro defects, the length of the defect is detected and, the defects are classified to a linear defect and a lump defect.

Japanese Patent Application Laid-Open Publication No. 2009-180590 (patent document 2) describes that, using an apparatus for detecting a defect in a surface of a magnetic disk similar to that described in the patent document 1, the cycles of linear defects are detected to detect a wrinkled defect.

Further, Japanese Patent Application Laid-Open Publication No. 2006-352173 (patent document 3) describes a technique of classifying defects in accordance with a state of a distribution of defects obtained by testing the surface of a semiconductor wafer.

Defects linearly distributed include continuously linear defects and defects which are discretely distributed in a linear region. In the defect classifying method described in the patent document 1, although continuously linear defects can be detected as linear defects, detection of defects which are discretely distributed in a linear region (continuous scratch defect) so as to be discriminated from random micro defects is not considered. In the invention disclosed in the patent document 2, since increase/decrease in reflection light generated by mild roughness in the surface of a magnetic disk is detected, micro defects cannot be detected. Further, in the defect classifying method described in the patent document 3, only the defect position information is used. Consequently, it is difficult to select and process a defect point having a specific feature from defects obtained from the plural detectors.

SUMMARY

The present invention is to address the problems of the above-described related arts and provide a method and apparatus for inspecting a surface of a substrate, capable of classifying defects (linear scratch defects) which are discretely and linearly distributed in the surface of a substrate so as to be discriminated from micro defects which are distributed at random.

To achieve the object, according to an aspect of the present invention, there is provided a substrate surface inspecting apparatus including: a rotatable stage on which a substrate to be inspected is placed; an inspection optical system having one or more illumination light sources for emitting light to a substrate placed on the stage and one or more detectors for detecting reflection/scattering light from the substrate which is irradiated with the light from the illumination light sources; an A/D converter for amplifying and A/D converting signals output from the one or more detectors in the inspection optical system; and a defect detector for detecting defects in a surface of the substrate by processing signals output from the one or more detectors and converted by the A/D converter and classifying the defected defects. The defect detector extracts micro defects in the surface of the substrate by processing the signals output from the one or more detectors, and detects linear defects existing discretely in a linear region from the extracted micro defects.

To achieve the object, according to another aspect of the present invention, there is provided a method for inspecting a surface of a substrate, including the steps of: emitting one or more illumination beams from one or more illumination light sources to a substrate placed on a rotatable stage while rotating the stage; detecting reflection/scattering light from the substrate which is irradiated with the light from the one or more illumination light sources by one or more detectors; amplifying and A/D converting signals output from the one or more detectors which have detected the reflection/scattering light from the substrate; detecting defects in a surface of the substrate by processing the A/D converted signals output from the one or more detectors; and classifying the defected defects. In the step of detecting the defect, micro defects in the surface of the substrate are extracted by processing the signals output from the one or more detectors and, in a step of classifying the detected defects, linear defects existing discretely in a linear region are detected from the extracted micro defects.

According to the aspects of the present invention, defects which occur linearly and discretely in a surface of a substrate of a magnetic disk can be detected as linear defects so as to be distinguished from defects which occur at random.

By grasping the shapes of the detected defects which occur linearly and discretely in the surface of a magnetic disk and the occurrence positions in the substrate of the magnetic disk, places as causes of defects in a manufacturing process can be narrowed down.

These features and advantages of the invention will be apparent from the following more particular description of preferred embodiments of the invention, as illustrated in the accompanying drawings.

BRIEF DESCRIPTION OF THE DRAWINGS

FIGS. 5A and 5B are diagrams showing an example of linear defects discretely existing in a linear region, which are extracted from detected micro defects;

FIGS. 6A and 6B are diagrams showing an example of linear defects discretely existing in a curved region, which are extracted from defected micro defects;

FIG. 7 is a flowchart of a modification of the processes for detecting and classifying defects shown in FIG. 2.

DESCRIPTION OF THE PREFERRED EMBODIMENTS

An embodiment of the present invention will be described below with reference to the drawings.

Figure 1:
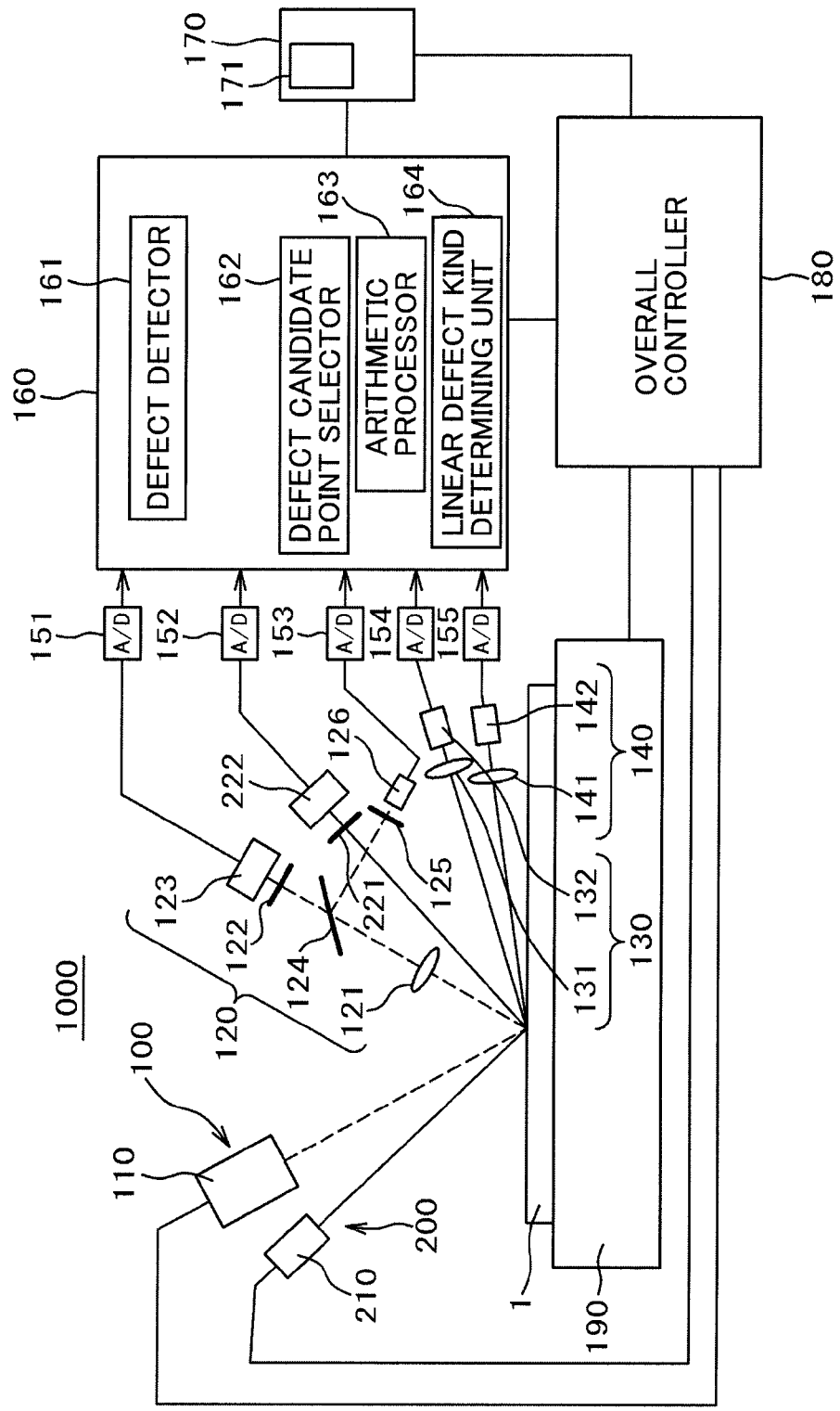
FIG. 1 is a block diagram showing a general schematic configuration of a surface inspecting apparatus as an embodiment of the present invention.

FIG. 1 shows a schematic configuration of an apparatus 1000 for inspecting a surface of a magnetic disk according to an embodiment. The apparatus 1000 for inspecting a surface of a magnetic disk has two illumination detection optical systems (hereinbelow, called optical systems). A first optical system 100 has one illuminating unit and three detecting units. The illuminating unit is a first illuminating unit 110 for emitting a laser beam having a first wavelength to the surface of a magnetic disk as a sample 1 from a high-angle direction. The three detecting units are a high-angle detecting unit 120, an intermediate-angle detecting unit 130, and a low-angle detecting unit 140.

The high-angle detecting unit 120 has a lens 121 condensing reflection/scattering light including regular-reflection light which travels in a high-angle direction out of directions indicated by broken lines, emitted from the first illuminating unit 110 and reflected/scattered by the surface of the sample 1, a wavelength selection filter 122 which transmits light having the same wavelength as that of the laser beam emitted from the first illuminating unit 110 in the light condensed by the condenser lens 121 and blocks light having different wavelengths, a high-angle detector 123 for detecting the light which passed through the wavelength selection filter 122, a mirror 124 for reflecting the regular reflection light from the sample 1 in the light condensed by the condenser lens 121, a wavelength selection filter 125 which transmits light having the same wavelength as that of the laser beam emitted from the first illuminating unit 110 in the regular reflection light from the sample 1 reflected by the mirror 124 and blocks light having different wavelengths, and a regular-reflection light detector 126 for detecting the light which passed through the wavelength selection filter 125.

The intermediate-angle detecting unit 130 has a condenser lens 131 for condensing scattering light which travels in an intermediate-angle direction in the light emitted from the first illuminating unit 110 and reflected/scattered by the surface of the sample 1, and an intermediate-angle detector 132 for detecting the light condensed by the condenser lens 131.

The low-angle detecting unit 140 has a condenser lens 141 for condensing scattering light which travels in a low-angle direction in the light emitted from the first illuminating unit 110 and reflected/scattered by the surface of the sample 1, and a low-angle detector 142 for detecting the light condensed by the condenser lens 141.

A second optical system 200 has one illuminating unit and one detecting unit. The illuminating unit of the second optical system 200 is a second illuminating unit existing in a plane different from that of the first optical system 100 and emitting a laser beam having a second wavelength to the surface of the magnetic disk as the sample 1 from an oblique direction. The detecting unit of the second optical system 200 has a detector 222 for detecting light passed through a pinhole device 221 in regular-reflection light which travels in a direction indicated by the solid line in light condensed/diffused by the roughness of the surface of the sample 1 in the laser beam emitted from the second illuminating unit 210. Signals output from the detectors 123, 222, 126, 132, and 142 are amplified and A/D converted by A/D converters 151, 152, 153, 154, and 155, respectively, and the resultant digital signals are supplied to a processor 160.

The processor 160 has: a defect detector 161 for receiving the A/D converted signals output from the detectors 123, 222, 126, 132, and 142 and detecting a micro defect; a defect candidate point selector 162 for receiving a signal from the defect detector 161, determining the kind of the micro defect and selecting a defect candidate point; an arithmetic processor 163 for receiving a signal from the defect candidate point selector 162 and performing arithmetic process on the signal; and a linear defect kind determining unit 164 for receiving a result of the process performed by the arithmetic processor 163 and determining the kind of a linear defect.

To the processor 160, an input/output unit 170 having a display screen 171 is connected. The processor 160 and the input/output unit 170 are connected to an overall controller 180. The overall controller 180 controls a stage unit 190 having a stage on which the sample 1 is placed and which rotates the sample 1 and is movable at least in one direction in a plane in which the sample 1 rotates.

With the above-described configuration, under control of the overall controller 180, the sample 1 on the stage unit 190 is rotated around the normal to the surface of the sample 1 as a rotation center, and starting to move at constant speed in a direction orthogonal to the normal.

In this state, a laser beam having a first wavelength is emitted from the first illuminating unit 110 in the first optical system 100 to the surface of the sample 1 which is on the rotating stage of the stage unit 190. Also from the second illuminating unit 210 in the second optical system 200, a laser beam having a second wavelength is emitted to a region irradiated with the first laser beam in the surface of the sample 1 which is on the rotating stage of the stage unit 190.

The optical path of a regular-reflection-light component in the light condensed by the condenser lens 121 is bent by the mirror 124 toward the detector 126. Light obtained by removing the regular-reflection light in the light condensed by the condenser lens 121 (scattering light around the optical axis of the regular-reflection light) enters the wavelength selection filter 122. The light of the component having the same wavelength as that of the first laser beam passes through the wavelength selection filter 122 and light of the other wavelength components is blocked by the wavelength selection filter 122. The light from which the regular-reflection light is eliminated and passed through the wavelength selection filter 122 is incident on the detector 123 and detected.

On the other hand, only light components having the same wavelength as that of the first laser beam in the regular-reflection-light component whose optical path is bent by the mirror 124 toward the detector 126 pass through the wavelength selection filter 125, and the light of the other wavelength components are blocked by the wavelength selection filter 125. The regular-reflection light which passed through the wavelength selection filter 125 is incident on the detector 126. That is, the laser beam emitted from the second illuminating unit 210 and reflected/scattered from the sample and condensed by the condenser lens 121 is blocked by the wavelength selection filters 122 and 125 and is not detected by any of the detectors 123 and 126.

The second optical system 200 is disposed at an angle different from the angle of the first optical system 100 in plan view in which the magnetic disk as the sample 1 is seen in a circular shape so that the influences of the regular-reflection light components of the systems are ignorable.

The sample 1 is moved straight while being rotated and an inspection is conducted from the outer rim toward the inner rim of the sample 1 to inspect the entire surface of the sample 1. The sample 1 is put upside down by using a substrate turning mechanism (not shown) so that the rear face which is not inspected yet faces upward. By conducting an inspection similar to that on the surface, both faces of the sample can be inspected.

In the embodiment, the wavelength selection filters 122 and 125 are used as optical elements in the optical path in the first optical system 100. Instead of them, an optical mask filter (including a pinhole device) or a polarization filter may be used singularly or together with a wavelength selection filter to make light of a specific component pass.

Figure 2:
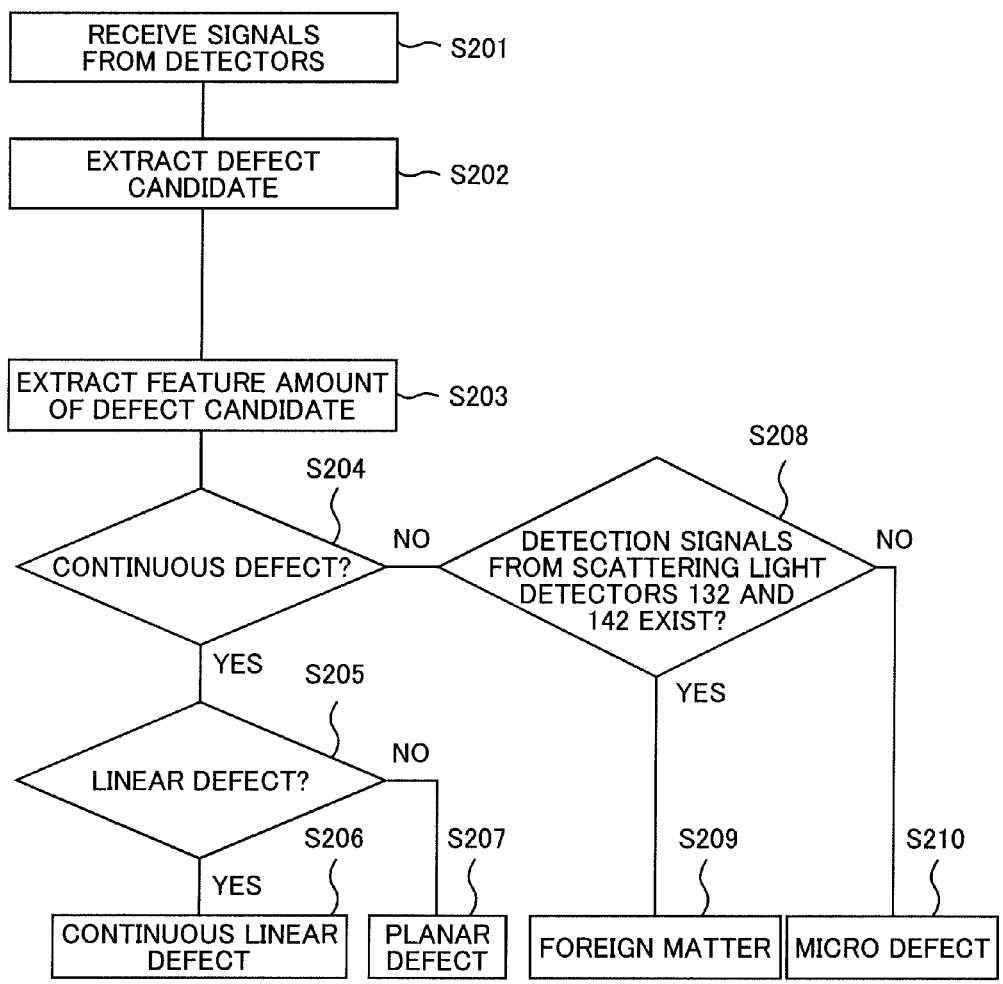
FIG. 2 is a flowchart of processes for detecting and classifying a defect in the embodiment of the invention.

Next, the flow of processes performed to detect a defect in the surface of the sample 1 by using the inspection apparatus shown in FIG. 1 will be described with reference to FIG. 2.

First, the sample 1 is continuously moved in one direction while being rotated by the stage unit 190. In this state, a first laser beam emitted from the first illuminating unit 110 in the first optical system 100 and a second laser beam emitted from the second illuminating unit 210 in the second optical system 200 are illuminating an inspection portion on the surface of the sample 1.

The reflection/scattering light generated by the sample 1 by the irradiation of the first and the second laser beams is detected by the high-angle detecting unit 120, the intermediate-angle detecting unit 130 and the low-angle detecting unit 140 in the first optical system 100, and the detecting unit in the second optical system 200. The detection signals output from the detectors 123, 222, 126, 132, and 142 are amplified and A/D converted by the A/D converters 151, 152, 153, 154, and 155, respectively, and the A/D converted signals are supplied to the processor 160 (S201).

The defect detector 161 extracts a defect candidate from the detection signals supplied from the detectors to the processor 160 (S202). A feature amount of the extracted defect candidate is calculated (S203), and defects which are continuous on the surface of the sample are extracted on the basis of the calculated feature amounts (S204). Whether the extracted defects are linear or not is determined (S205). When it is determined that the defects are linear, the defects are determined as continuous linear defects (S206). When it is determined that the defects are not linear but are spread, the defects are determined as planar defects (S207). Subsequently, a check is made to see whether or not the defect which is determined as a discontinuous defect in S204 is detected by the detector 132 of the intermediate-angle detecting unit 130 and the detector 142 of the low-angle detecting unit 140 (S208). When it is detected, the defect is determined as a foreign matter (S209). When it is not detected, the defect is determined as a micro defect (S210).

Figure 3:
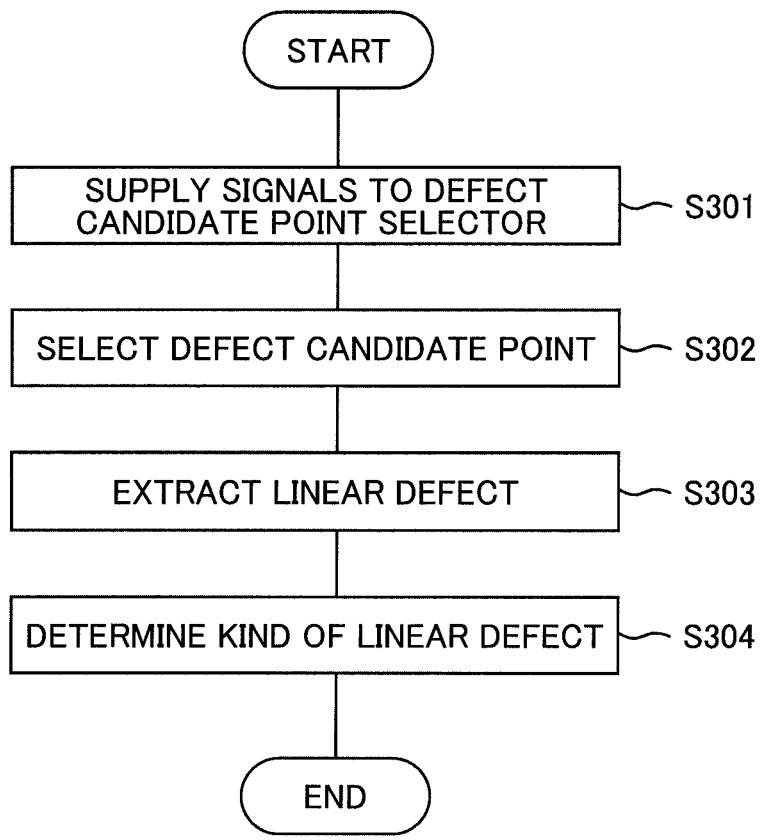
FIG. 3 is a flowchart of processes for extracting linear defects existing discretely in a linear region from micro defects in the embodiment of the invention.

The flow of processes of extracting linear defects which are discretely distributed in a linear small region from defects determined as micro defects in S210 will now be described with reference to FIG. 3.

First, a signal of a defect determined as a micro defect in S210 is sent together with information of the feature amount which is calculated in S203 to the defect candidate point selector 162 (S301). The detected micro defects are distributed on the disk plane by using position information, and kinds of defects which are components of one of linear defects are selected (S302). The number of kinds of defects to be selected is not limited to one but plural kinds may be selected. In case of selecting the classified defect kinds, a micro defect group forming linear defects may be selected by directly designating a light reception condition of the detectors.

The information of the selected defect kind or the micro defect group is sent to the arithmetic processor 163. Using the data of the position of each of the micro defects, defect candidates existing linearly are extracted from them by, for example, a Hough transform process (S303).

Figure 4A:
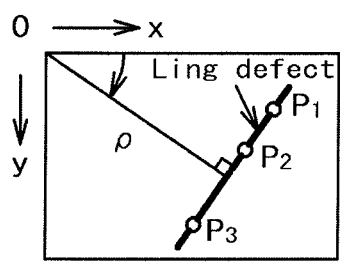
FIGS. 4A and 4B are diagrams for explaining the principle of the Hough transform.
Figure 4B:
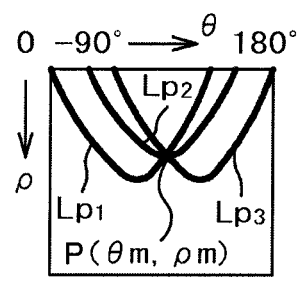

As shown in FIG. 4A, the Hough transform determines a straight line on which feature points (the positions of defects in the embodiment) exist the most. For example, angle θ to the x axis formed by a normal extending from the point θ to a straight line connecting two points P1 and P2 and length ρ of the normal are sequentially calculated for each of straight lines connecting two points, and are plotted to a two-dimensional space as shown in FIG. 4B. A straight line expressed by a set of the length ρ and the angle θ determined by a point P(θm, ρm) as a crossing point is determined as the straight line on which feature points exist most.

By the Hough transform, even when distributions of points which construct a line are discontinuous, the line on which the points exist can be detected. The Hough transform is effective to extract linear defect components from defect points which exist discretely.

In the Hough transform process, a line on which at least a predetermined number of defect points exist is detected. In consideration of positional errors in detecting defect candidates, as shown in FIGS. 5A and 5B, defect points existing within a distance "w" of a margin of a detected straight line are regarded as linear defect points, and the total number of linear defect points and defect density are calculated including the regarded defect points.

Using a line end at which the defect density is equal to or less than a predetermined value as a defect end point, the length and position of the linear defect candidates are determined. From the determined linear defect candidates, defects are determined on the basis of spatial feature amounts such as length, position, and density.

The process is not limited to detection of defects in a straight line shape. By defining a circle or a circular arc, or a figure indicated by an arbitrary function using the generalized Hough transform, for example, as shown in FIGS. 6A and 6B, micro defects in a curved-line shape along the defined shape and the center position of the curvature of the curved line can be detected.

By performing the process as described above, even linear defects formed by a group of discrete points can be detected so as to be discriminated from other random defects.

To shorten the process time, a detection shape condition may be limited in advance in accordance with a process condition. In the case where the correspondence between a geometric shape of a detected defect and a defect generating process is determined empirically or logically, it may be formulated and a determination may be made by using the formula.

The data processed by the arithmetic processor 163 is sent to the linear defect kind determining unit 164, and the kind of the linear defect is determined on the basis of the physical shape of the detected linear defect (S304). For example, when a line to be detected is a circular or a circular arc, the center point of the circle or the circular arc and the radius are also calculated as geometric feature amounts.

Although the discrete defect points are classified to a foreign matter or a micro defect depending on the presence or absence of a detection signal of the scattering light detection system in S208, they may not be classified in S208. In 5303, whether defects (random defects) which are not determined as candidates existing in a linear shape may be determined as foreign matters or not on the basis of the condition of S208.

The defects determined as continuous linear defects in S206 may be supplied together with the micro defect in S210 to the defect candidate point selector in S301. In such a manner, the defects as linear defects generated by the same source and having the features classified to the continuous part and the discrete part can be detected as a single defect. The flow of the modification is shown in FIG. 7.

The flow of FIG. 7 will be described.

First, the sample 1 is continuously moved in one direction while being rotated by the stage unit 190. In this state, a first laser beam emitted from the first illuminating unit 110 in the first optical system and a second laser beam emitted from the second illuminating unit 210 in the second optical system 200 are illuminating an inspection portion on the surface of the sample 1. The reflection/scattering light generated by the sample 1 by the irradiation of the first and the second laser beams is detected by the high-angle detecting unit 120, the intermediate-angle detecting unit 130 and the low-angle detecting unit 140 in the first optical system 100, and the detecting unit in the second optical system 200. The detection signals output from the detectors 123, 222, 126, 132, and 142 are amplified and A/D converted by the A/D converters 151, 152, 153, 154, and 155, respectively, and the A/D converted signals are input to the processor 160 (S701).

The defect detector extracts a defect candidate from the detection signals input from the detectors to the processor 160 (S702). A feature amount of the extracted defect candidate is calculated (S703), and defects which are extracted on the basis of the calculated feature amounts are determined whether continuous defects or not (S704). Then, the defects determined as continuous defects (YES in S704) are determined whether linear defects or not (S705). In the case of YES, the defects are determined as continuous linear defects (S706). In the case of NO, the defects are determined as planar defects (S707). On the other hand, a defect which is determined as a discontinuous defect (NO) in S704 is classified as a micro defect (S708), and the information of the micro defect is supplied to the defect candidate point selector 162 (S709). A defect candidate point is selected from the information of the micro defect which is supplied to the defect candidate point selector 162 and the defects determined as continuous linear defects in S706 (S710). The linear defects are extracted from the information of the defect candidate points (S711), and the kind of the extracted linear defects is determined (S712).

By selecting the defect candidate points from both of the micro defects as discontinuous defects and the continuous linear defects, defects as linear defects generated by the same source and separated to the continuous part and the discrete part can be detected as a single defect. On the other hand, the defects which are not extracted as linear defects in S711 are determined as nonlinear (random) defects. The input signals are checked to see whether or not there are detection signals from the scattering light detection systems 132 and 142 on the nonlinear defects (S713). In the case where there are detection signals from the scattering light detection systems 132 and 142, the micro defects are determined as foreign matters (S714). On the other hand, in the case where there are no detection signals from the scattering light detection systems 132 and 142, the defect is determined as a small flaw in the surface of the substrate (S715).

Generally, in a magnetic disk polishing process, while making a lower board having a top face to which a donut-shaped grinder is attached rotate, an upper board having an under face to which a grinder is attached is made rotate and revolve, the top and under faces of a magnetic disk substrate sandwiched by the grinders are polished by the grinders. The configuration of such a polishing apparatus is described in, for example, Japanese Patent Application Laid-Open Publication No. H04-013553. Since the magnetic disk substrate is polished in such a manner, the size and the center position of an arc of linear defects caused in the polishing process are limited to a certain degree. Consequently, whether the center point of the arc of the defects is the center of the magnetic disk or not is determined. In the case of NO, a defect source process can be estimated depending on whether the center point of the arc of the defects is in the plane of the magnetic disk or on the outside. In the case where the center point of the arc coincides or almost coincides with the center of the magnetic disk, the defect can be estimated as a defect caused by a head touch. Obviously, defect which occurs in the process such as a defect which occurs in handling the substrate can be estimated.

Figure 8:
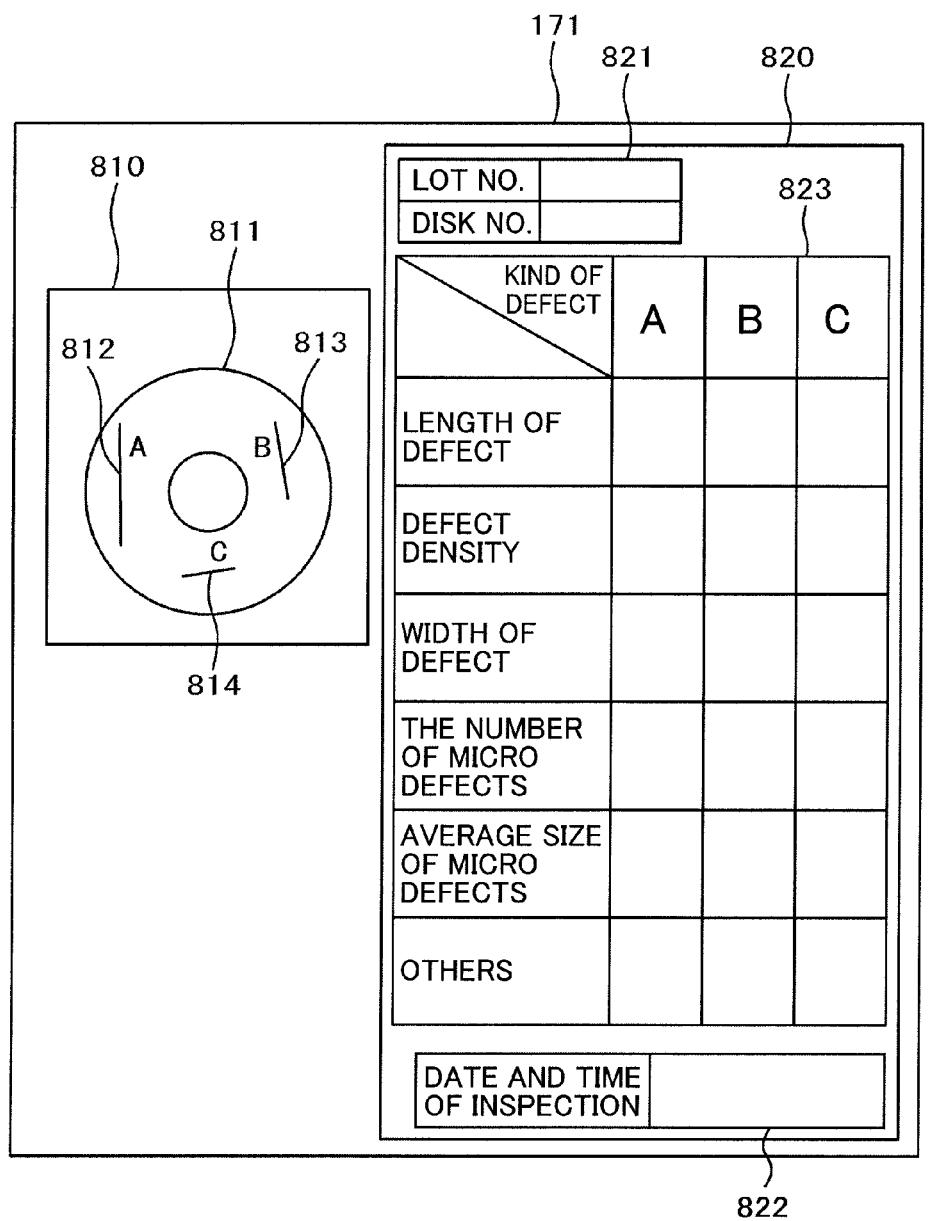
FIG. 8 is a front view of a display screen for displaying a result of linear defects extracted in the embodiment of the invention.

FIG. 8 illustrates an example of the screen 171 of the input/output unit 170 for outputting a result of detection of discrete linear defects detected in the embodiment.

The screen 171 outputting an inspection result includes a defect map display region 810 showing the positions on the magnetic disk, of detected linear defects in a map form, and a data display region 820 displaying data related to the detected linear defects. In the defect map display region 810, a linear defect A 812, a linear defect B 813, and a linear defect C 814 are displayed by kinds of the linear defects detected in an outline 811 of the magnetic disk. The data display region 820 includes a region 821 displaying disk information such as lot No. and disk No. of a magnetic disk to be inspected, a region 822 displaying date and time of an inspection, and a region 823 displaying information on a linear defect such as length of each linear defect, defect density, defect width (width W in FIG. 4), the number of micro defects, and average size of micro defects.

In the embodiment, micro defects which are discretely detected are extracted from defect signals obtained from detection signals of reflection/scattering light from the surface of a magnetic disk. From the extracted discrete defects, linear defects (in straight line and curved line) existing in linear regions can be detected. Therefore, linear defects having relatively low density, which occur in a magnetic disk manufacturing process can be detected at higher sensitivity.

Although the present invention achieved by the inventors herein has been concretely described above on the basis of the embodiments, obviously, the present invention is not limited to the foregoing embodiments but can be variously modified without departing from the gist.

The invention may be embodied in other specific forms without departing from the spirit or essential characteristics thereof. The present embodiments are therefore to be considered in all respects as illustrative and not restrictive, the scope of the invention being indicated by the appended claims, rather than by the foregoing description, and all changes which come within the meaning and range of equivalency of the claims are therefore intended to be embraced therein.

The invention claimed is:

1. A substrate surface inspecting apparatus comprising:
   a rotatable stage on which a substrate to be inspected is placed;
   an inspection optical system having one or more illumination light sources configured to emit light to a substrate placed on the stage, and one or more detectors configured to detect reflection/scattering light reflected or scattered from the substrate irradiated with light from the illumination light sources;

an A/D converter configured to amplify and to A/D convert signals output from the one or more detectors in the inspection optical system; and a defect detector configured to detect defects existing in a surface of the substrate, by processing signals output from the one or more detectors and converted by the A/D converter, and to classify the defected defects, wherein the defect detector is configured to extract defects existing in the surface of the substrate, including micro defects, by processing the signals output from the one or more detectors, to detect continuous linear defects, and to detect, from the extracted micro defects, discrete linear defects that exist in a linear region of the surface of the substrate.

2. The substrate surface inspecting apparatus according to claim 1,
wherein more than one illumination light sources are configured to emit laser beams to the substrate; and
wherein laser beams from at least one of said more than one illumination light sources has a different wavelength than laser beams emitted from a different at least one of said more than one illumination light sources.

3. The substrate surface inspecting apparatus according to claim 2, wherein the defect detector is configured to detect discrete linear defects existing in a curved region of the surface of the substrate, based on the extracted micro defects and a center position of curvature of the curved region.

4. The substrate surface inspecting apparatus according to claim 2, further comprising:
an output unit configured to output information, including feature amounts, regarding discrete linear defects detected by the defect detector, the discrete linear defects existing in a linear region of the surface of the substrate.

5. The substrate surface inspecting apparatus according to claim 1, wherein the defect detector is configured to detect discrete linear defects existing in a curved region of the surface of the substrate, based on the extracted micro defects and a center position of curvature of the curved region.

6. The substrate surface inspecting apparatus according to claim 1, further comprising:
an output unit configured to output information, including feature amounts, regarding discrete linear defects detected by the defect detector, the discrete linear defects existing in a linear region of the surface of the substrate.

7. A method for inspecting a surface of a substrate, comprising the steps of:

emitting one or more illumination beams from one or more illumination light sources to a substrate placed on a rotatable stage, while rotating the rotatable stage;

detecting, by use of one or more detectors, reflection/scattering light reflected or scattered from the substrate irradiated with illumination beams from the one or more illumination light sources;

amplifying and A/D converting signals output from the one or more detectors which have detected the reflection/scattering light reflected or scattered from the substrate;

detecting defects existing in a surface of the substrate, by processing the A/D converted signals output from the one or more detectors, wherein the step of detecting defects includes extracting micro defects existing in the surface of the substrate, by processing the signals output from the one or more detectors; and classifying the detected defects, into categories including continuous linear defects and discrete linear defects, wherein discrete linear defects exist in a linear region of the surface of the substrate and are detected based on the extracted micro defects.

8. The method for inspecting a surface of a substrate according to claim 7, wherein the one or more illumination beams emitted to the substrate include a laser beam with a different wavelength than other laser beams.

9. The method for inspecting a surface of a substrate according to claim 8, wherein the step of classifying the detected defects includes detecting discrete linear defects existing in a curved region of the surface of the substrate, based on the extracted micro defects and a center position of curvature of the curved region.

10. The method for inspecting a surface of a substrate according to claim 7, wherein the step of classifying the detected defects includes detecting discrete linear defects existing in a curved region of the surface of the substrate, based on the extracted micro defects and a center position of curvature of the curved region.

11. The method for inspecting a surface of a substrate according to claim 7, further comprising:
outputting information, including feature amounts, regarding discrete linear defects existing in a linear region of the surface of the substrate, that were detected in the step of classifying the detected defects.

12. The method for inspecting a surface of a substrate according to claim 8, further comprising:
outputting information, including feature amounts, regarding discrete linear defects existing in a linear region of the surface of the substrate, that were detected in the step of classifying the detected defects.

* * * * *